US00PP08788P

United States Patent [19]

Marousky et al.

[11] Patent Number: Plant 8,788

[45] Date of Patent: Jun. 14, 1994

[54] BAHIAGRASS PLANT MBA-1

[75] Inventors: Francis J. Marousky; Albert E. Dudeck, both of Gainesville, Fla.

[73] Assignee: University of Florida, Gainesville, Fla.

[21] Appl. No.: 999,236

[22] Filed: Dec. 31, 1992

[51] Int. Cl.[5] ..... A01H 5/00

[52] U.S. Cl. ..... Plt./90

[58] Field of Search ..... Plt. 90

*Primary Examiner*—James R. Feyrer

*Attorney, Agent, or Firm*—Saliwanchik & Saliwanchik

[57] ABSTRACT

A new variety of dwarf bahiagrass having desirable characteristics of slow growth and short leaves and inflorescences (seed heads). The new variety would be especially useful to reduce maintenance costs and retain aesthetics for roadside growth and home lawns.

2 Drawing Sheets

SUMMARY OF THE INVENTION

The new and distinct variety of bahiagrass, (Paspalum notatum Flugge) developed in Gainesville, Fla., at the C.C. Horn Turfgrass Field Laboratory at the University of Florida Environmental Horticulture Department, was initially selected from a population of seedlings derived from a cross of an isolated group of "Semi-dwarf" vegetatively propagated plants with small to medium inflorescences. Seedlings were spaced planted (1 m×1 m) in field plots in March and subsequently evaluated for growth and flowering characteristics from May to October. One plant (the variety described herein as MBA-1 bahiagrass) had a slow growth rate from underground rhizomes with dwarf morphological characteristcs and did not flower during the first summer evaluation.

The plant was vegetatively propagated in late October and the daughter plants were grown in a greenhouse over winter. The following spring, the plants were placed in field plots and evaluated for growth and flowering characteristics.

Typically, common (wild) and named cultivars (varieties) of bahiagrass produce tall inflorescences (seed heads) in abundant numbers (Table 1). Seed heads of these wild or named cultivars are about 60 cm tall and are produced from early May to mid-September. The tall seed heads are a nuisance in the home lawn and roadsides because of the continual maintenance required. In order to keep the appearance of the grass aesthetically pleasing, frequent mowing is necessary to remove seed heads.

A dwarf bahiagrass with limited flowering capability and short inflorescences has potentially wide use for home lawns, roadsides, and canal banks. Reduction in mowing frequency is one of the primary advantages of the subject MBA-1 bahiagrass variety. Labor and money expenditure could be significantly reduced if less maintenance were required.

A Florida Department of Agriculture survey in 1974 estimated that 319,000 acres of bahiagrass (41% of the total acreage) were maintained as lawn grass excluding roadsides and sod production. Bahiagrass sod production totaled 10,525 acres, which was 34% of the total acreage. There are no recent reports available which indicate maintenance costs of home lawns; however, a Florida Department of Agriculture survey in 1974 indicated that $344 million per annum was expended in the care of home lawns.

At present, there are about 11,500 miles (approximately 100,000 acres) of primary roadsides in Florida planted wtih bahiagrass. According to Florida Department of Transportation estimates, these roadsides are mowed four to five times each year at a cost which averages $100–180 per acre. Roadsides planted with the bahiagrass variety described and claimed herein could be easily be maintained with a single mowing per year, which could translate to a minimum savings to Florida taxpayers of $7 million per year. Thus, the disclosed MBA-1 bahiagrass of limited flowering capacity would have major economic impact because of reduced energy and labor to maintain this popular turfgrass.

The most distinctive features of MBA-1 bahiagrass herein are its relatively slow growth rate, limited leaf elongation, and production of relatively few seed heads, which are short and inconspicuous.

Asexual reproduction by us or under our direction of the new bahiagrass variety, as performed in Gainesville, Fla., shows that the described morphological characteristics come true to form and are established and transmitted through secondary propagation as sprigs or sod. The MBA-1 variety can be commercially used by cultivating sprigs (plugs) or sod and sold in these forms.

BRIEF DESCRIPTION OF THE DRAWINGS

The accompanying drawings are photographs of the new claimed bahiagrass cultivar MBA-1 illustrating its distinctive characteristics.

DETAILED DESCRIPTION OF THE NEW VARIETY

Figure 1:
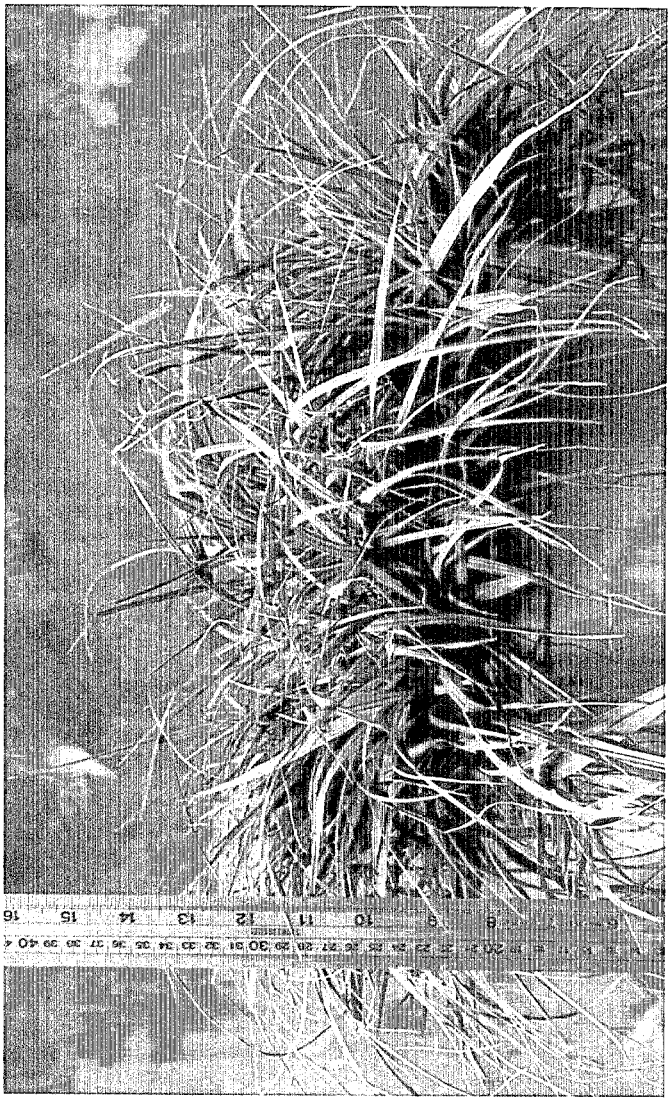
FIG. 1 shows a plant grown for one year in a 20 cm pot. The figure illustrates the height and overall dwarf characteristics of the plant. The plant was originally propagated from a single rhizome, lightly fertilized, and not trimmed during the one-year growth period.

The following is a detailed description of the new variety of bahiagrass with color terminology in accordance with Munsell Color notations. Wherein dimension, sizes, and other characteristics are given, it is to be understood that such characteristics are approximations of averages set forth as accurately as practicable. The description herein is from specimens grown in 1.5×1.8 m plots in Gainesville, Fla., in summer, 1990.

Name: MBA-1 Bahiagrass.

Plant: Growth habit is that of a true dwarf.

Leaf growth:

*Spring.*—The subject plant, grown as a turf and mowed to a height of 10 cm in early May, grew little (approximately 0.5 cm) in 3 weeks while the cultivar Pensacola grew to a height of 38 cm (28 cm above the mowed height of 10 cm) or approximately 9 cm growth/week.

*Summer.*—Plants mowed to a height of 10 cm grew to a height of 12 cm in one week (approximately 2 cm growth/week) while Pensacola grew to 18 cm (approximately 8 cm growth/week). Length of leaf blades in MBA-1 bahiagrass averaged 14 cm and was approximately equal to that of the B-1 bahiagrass (Table 1). The subject MBA-1 bahiagrass had shorter leaf blades than the Argentine and Pensacola cultivars which averaged 20 and 29 cm, respectively. Width of leaf blades in MBA-1 averaged about 6 mm and was approximately equal to that of Argentine bahiagrass. B-1 bahiagrass had the widest leaf blade width of nearly 8 mm while Pensacola bahiagrass and the narrowest leaf blade with a width about of 4 mm. Comparative leaf morphologies for the subject MBA-1 cultivar and Argentine, B-1, and Pensacola cultivars are shown in Table 1, below:

TABLE 1

Comparative leaf morphology of bahiagrass cultivars when grown in unmowed pot cultures in a glass house in Gainesville, Florida

| Cultivar | Length (cm) | Width (mm) |
|---|---|---|
| Argentine | 19.9 ± 1.6 | 5.8 ± 0.6 |
| B-1† | 13.1 ± 2.9 | 7.6 ± 0.6 |
| MBA-1 | 14.2 ± 2.2 | 5.9 ± 0.9 |
| Pensacola | 29.2 ± 3.1 | 3.5 ± 0.5 |

† Data from U.S. Plant Patent 7,429.

Number and size: MBA-1 bahiagrass produced less than one seedhead per square meter per week during the 1990 summer period, whereas Argentine and Pensacola bahiagrasses produced 7 and 11 seedheads per square meter per week, respectively (Table 2). Seedhead height for MBA-1 bahiagrass averaged 16 cm and was approximately equal to that of B-1 bahiagrass. Argentine and Pensacola bahiagrasses had the tallest seedheads which averaged 46 and 55 cm, respectively. Number of racemes per inflorescences averaged 2.2 and was similar to the other cultivars (Table 2). However, length of racemes in MBA-1 bahiagrass averaged 46 mm, which was shorter than raceme length in Argentine and Pensacola bahiagrass, which averaged 68 and 109 mm, respectively. Comparative flowering characteristics for the bahiagrass cultivars MBA-1, and Pensacola are shown in Table 2, below.

TABLE 2

Comparative flowering characteristics of bahiagrass cultivars at Gainesville, Florida

| | Inflorescence | | Racemes per inflorescence | |
|---|---|---|---|---|
| Cultivar | Height (cm) | Number | Number | Length (mm) |
| Argentine | 46 ± 4 | 6.6 ± 3.3 | 2.1 ± 0.3 | 68 ± 9 |
| B-1†† | 18 ± 2 | — | 2 or 3 | — |
| MBA-1 | 16 ± 2 | 0.5 ± 0.5 | 2.3 ± 0.5 | 46 ± 6 |
| Pensacola | 55 ± 6 | 11.1 ± 3.4 | 2.1 ± 0.3 | 109 ± 20 |

† Average per square meter per week from July-September 1990.
†† Data from U.S. Plant Patent No. 7,429.

Flowering capacity: Limited production for 7 to 8 weeks commencing in early July and completion in late August. Argentine and Pensacola bahiagrasses produced many seedheads for up to 20 weeks from late May to late October.

Figure 2:
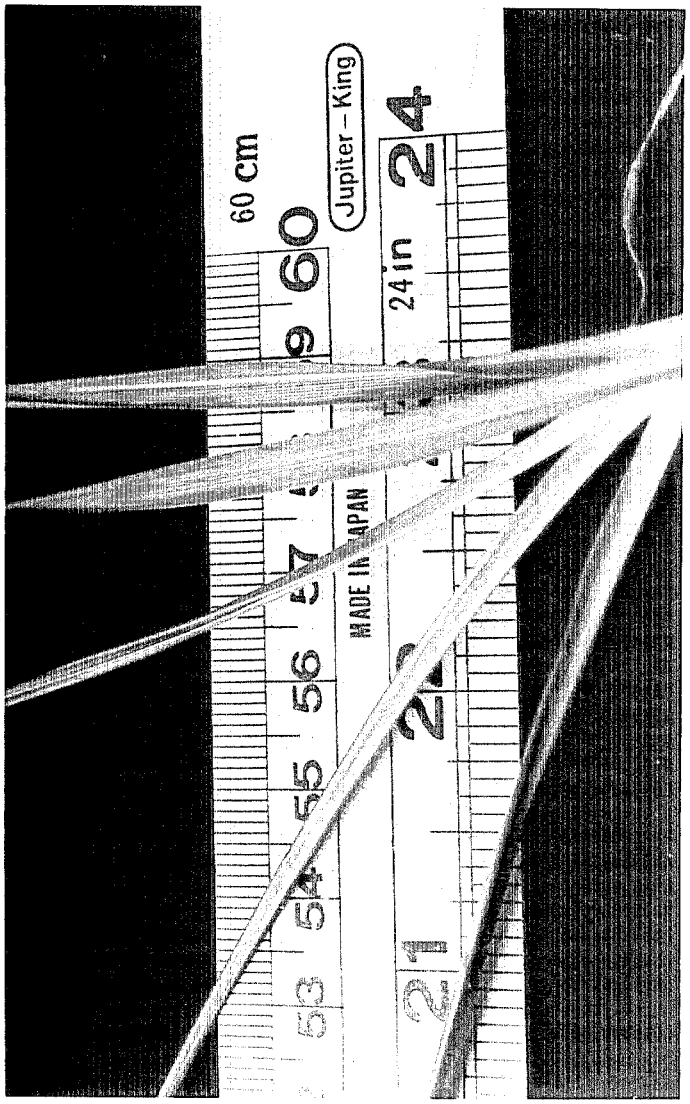
FIG. 2 shows the distinctive leaf width and length of the newly developing shoot.

The new variety is distinct from another variety of bahiagrass (see U.S. Plant Pat. No. 7,429) in that the variety described in U.S. Plant Pat. No. 7,429 has a prostrate growth habit and mature leaves 7.6 mm wide and 13.1 cm long. Flowering culms of the patented variety are prostrate to decumbent. The new and distinct variety described herein is a true dwarf bahiagrass plant which, as described, produces few, short inflorescences for a limited time with leaves 5.9 mm wide and 14.2 mm long (see FIGS. 1 and 2). Typical leaf color is 10.0 GY 5/6 (Munsell Color Notation) but varies depending on fertility, time of year, and other environmental variables.

We claim:

1. A new and distinct variety of dwarf bahiagrass, *Paspalum notatum* Flugge, designated MBA-1, as shown and described characterized by its slow growth rate, limited flowering capacity, short inflorescences, and distinctive leaf blade having color designation 10.0 GY S/6 (Munsell Color Notation) wherein said leaf blade is approximately 12 cm in length and 5.9 mm in width.

* * * * *

UNITED STATES PATENT AND TRADEMARK OFFICE

CERTIFICATE OF CORRECTION

PATENT NO. : Plant 8,788

DATED : June 14, 1994

INVENTOR(S) : Francis J. Marousky and Albert E. Dudeck

It is certified that error appears in the above-indentified patent and that said Letters Patent is hereby corrected as shown below:

Column 1, line 10: Delete "spaced planted" and insert --space planted--.

Column 2, line 10: Delete "could be easily be" and insert --could easily be--.

Column 3, line 26: Delete "bahiagrass and the" and insert --bahiagrass had the--.

Column 4, line 7: Delete "MBA-1, and Pensacola" and insert --MBA-1, Argentine, B-1, and Pensacola--.

Signed and Sealed this

Thirteenth Day of September, 1994

*Attest:*

*Attesting Officer*

BRUCE LEHMAN

*Commissioner of Patents and Trademarks*